(12) United States Patent
Lin et al.

(10) Patent No.: US 12,106,479 B2
(45) Date of Patent: Oct. 1, 2024

(54) ULTRASOUND IMAGE RECOGNITION SYSTEM AND DATA OUTPUT MODULE

(71) Applicant: T-JET Meds CORPORATION LIMITED, New Taipei (TW)

(72) Inventors: Ming-Chin Lin, New Taipei (TW); Lung Chan, New Taipei (TW)

(73) Assignee: T-JET Meds CORPORATION LIMITED, New Taipei (TW)

( * ) Notice: Subject to any disclaimer, the term of this patent is extended or adjusted under 35 U.S.C. 154(b) by 353 days.

(21) Appl. No.: 17/700,837

(22) Filed: Mar. 22, 2022

(65) Prior Publication Data

US 2023/0306597 A1    Sep. 28, 2023

(51) Int. Cl.
  *G06T 7/00*      (2017.01)
  *G16H 30/40*     (2018.01)
  *G06F 40/186*    (2020.01)

(52) U.S. Cl.
  CPC .......... *G06T 7/0014* (2013.01); *G16H 30/40* (2018.01); *G06F 40/186* (2020.01); *G06T 2207/10132* (2013.01); *G06T 2207/30104* (2013.01)

(58) Field of Classification Search
  CPC ........ G06T 7/0014; G06T 2207/10132; G06T 2207/30104; G16H 30/40; G06F 40/186
  See application file for complete search history.

(56) References Cited

U.S. PATENT DOCUMENTS

| | | | | |
|---|---|---|---|---|
| 6,160,610 A | * | 12/2000 | Toda ................. | B41J 2/473 347/240 |
| 2004/0028174 A1 | * | 2/2004 | Koren ................ | A61B 6/563 705/2 |
| 2007/0156917 A1 | * | 7/2007 | Hunt ................. | G16H 10/40 709/232 |
| 2008/0219599 A1 | * | 9/2008 | Hopkins ............. | H04N 23/64 382/312 |
| 2010/0321383 A1 | * | 12/2010 | Nakamura .......... | G06F 3/017 345/419 |

(Continued)

FOREIGN PATENT DOCUMENTS

| CN | 1542641 A | 11/2004 |
|---|---|---|
| CN | 106485037 A | 3/2017 |

(Continued)

*Primary Examiner* — Dominic E Rego
(74) *Attorney, Agent, or Firm* — Li & Cai Intellectual Property (USA) Office

(57) ABSTRACT

An ultrasound image recognition system and a data output module are provided. The ultrasound image recognition system includes an image analyzing device, a data processing device, and a data output module. The image analyzing device is configured to receive an image having a predetermined format. The image analyzing device generates a plurality of physiological image parameters. The data processing device is connected to the data processing device. The image analyzing device provides the plurality of physiological image parameters and the image having a predetermined format to the data processing device. The data processing device provides a comparison result of physiological parameter based on the plurality of physiological image parameters and a plurality of predetermined physiological image parameters. The data processing device converts the image having a predetermined format into an image having a first format.

7 Claims, 7 Drawing Sheets

(56) References Cited

U.S. PATENT DOCUMENTS

| | | | | |
|---|---|---|---|---|
| 2012/0242803 | A1* | 9/2012 | Tsuda | H04N 13/239 |
| | | | | 348/51 |
| 2014/0253919 | A1* | 9/2014 | Yui | G01B 9/02041 |
| | | | | 356/301 |
| 2015/0265248 | A1* | 9/2015 | Jin | A61B 8/469 |
| | | | | 600/440 |
| 2015/0288970 | A1* | 10/2015 | Park | H04N 19/177 |
| | | | | 375/240.13 |
| 2017/0032214 | A1* | 2/2017 | Krenzer | G06T 3/40 |
| 2017/0352284 | A1* | 12/2017 | Pao | G09B 5/08 |
| 2018/0271501 | A1* | 9/2018 | Wang | G01G 19/00 |
| 2018/0353151 | A1* | 12/2018 | Tang | A61B 6/545 |
| 2019/0033435 | A1* | 1/2019 | Sakai | G01S 7/52025 |
| 2019/0142388 | A1* | 5/2019 | Gonyeau | A61B 8/5223 |
| | | | | 600/407 |
| 2019/0209121 | A1 | 7/2019 | Miyachi et al. | |
| 2019/0313963 | A1* | 10/2019 | Hillen | G06V 10/764 |
| 2020/0077871 | A1* | 3/2020 | Ogihara | A61B 1/00059 |
| 2021/0173196 | A1* | 6/2021 | Langlois | G02B 21/06 |
| 2021/0245005 | A1* | 8/2021 | Pao | A63B 24/0006 |
| 2021/0282655 | A1* | 9/2021 | Rege | A61B 3/10 |
| 2021/0307038 | A1* | 9/2021 | Liu | H04B 7/0695 |
| 2021/0325860 | A1* | 10/2021 | Borrelli | G06N 3/08 |
| 2022/0284704 | A1* | 9/2022 | Lei | G06V 10/98 |

FOREIGN PATENT DOCUMENTS

| | | |
|---|---|---|
| CN | 107767928 A | 3/2018 |
| CN | 109688939 A | 4/2019 |

\* cited by examiner

ULTRASOUND IMAGE RECOGNITION SYSTEM AND DATA OUTPUT MODULE

FIELD OF THE DISCLOSURE

The present disclosure relates to an ultrasound image recognition system and data output module, and more particularly to a low-cost ultrasound imaging recognition system and data output module.

BACKGROUND OF THE DISCLOSURE

Conventionally, medical images require a significant amount of time for doctors to study and analyze. Furthermore, contents of an analysis report cannot be adjusted based on customer demands, so that a higher quality of service cannot be easily provided.

Therefore, how to provide an ultrasound image recognition system that is low cost and a data output module that is capable of correspondingly providing customized analysis contents so as to overcome the aforementioned deficiencies, has become an important issue to be addressed in the healthcare industry.

SUMMARY OF THE DISCLOSURE

In response to the above-referenced technical inadequacies, the present disclosure provides an ultrasound image recognition system. The ultrasound image recognition system includes an image analyzing device, a data processing device, and a data output module. The image analyzing device is configured to receive an image having a predetermined format. The image analyzing device generates a plurality of physiological image parameters based on the image having a predetermined format. The data processing device is connected to the image analyzing device. The image analyzing device provides the plurality of physiological image parameters and the image having a predetermined format to the data processing device. The data processing device provides a comparison result of physiological parameters based on the plurality of the physiological image parameters and a plurality of predetermined physiological image parameters, and converts the image having a predetermined format into an image having a first format. The data output module is connected to the data processing device. The data processing device provides the image having a first format, the plurality of physiological image parameters, the plurality of predetermined physiological image parameters, and the comparison result of physiological parameter to the data output module. The data output module provides an ultrasound image analysis report based on the image having a first format, the plurality of physiological image parameters, the plurality of predetermined physiological image parameters, and the comparison result of physiological parameter.

In one aspect, the present disclosure provides a data output module that includes an output controller and a storage unit. The output controller provides an analysis report based on a plurality of images and a plurality of parameters. The storage unit is connected to the output controller and storing a plurality of analysis report templates. Each of the plurality of analysis report templates includes a plurality of editing areas. When the plurality of images or the plurality of parameters are disposed in one of the plurality of editing areas of one of the plurality of analysis report templates, an image size, a text size and a table size of the plurality of images or the plurality of parameters are adjusted based on a size of the one of the plurality of editing areas.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
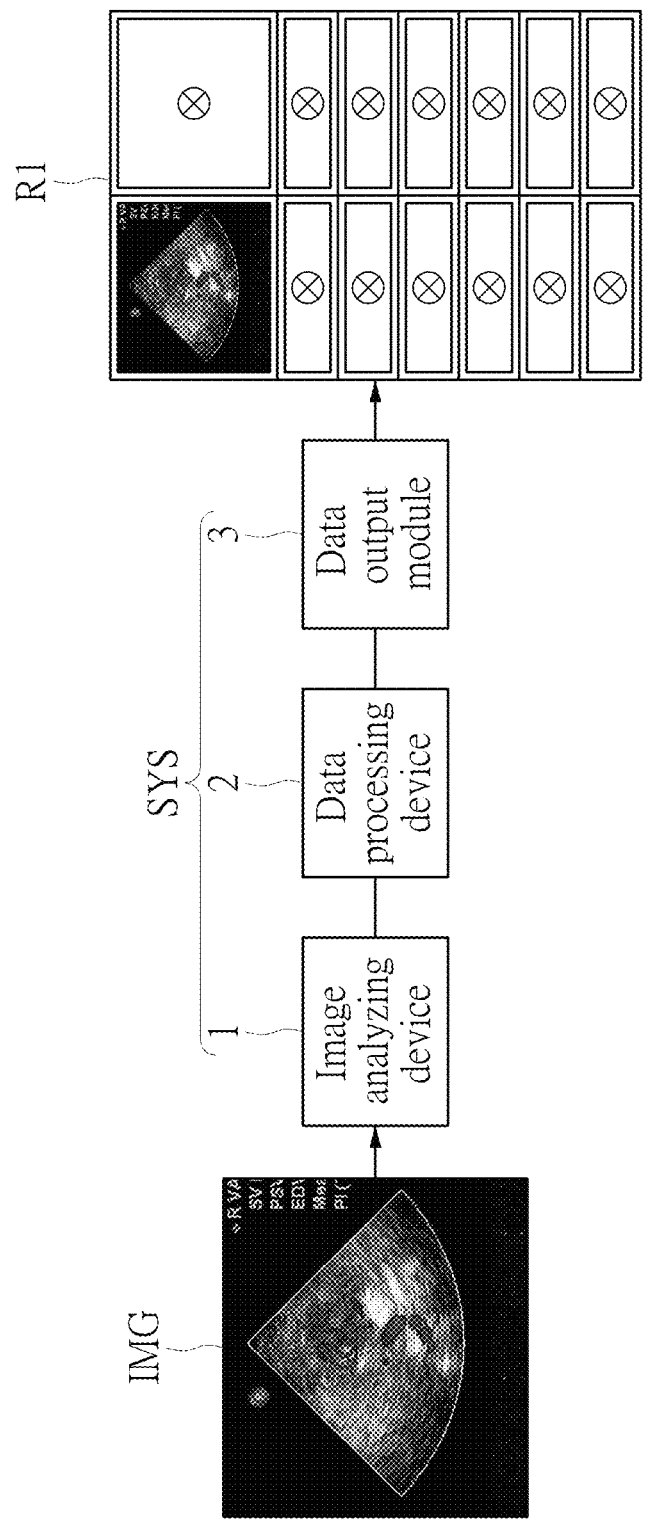
FIG. 1 is a functional block diagram of an ultrasound image recognition system according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
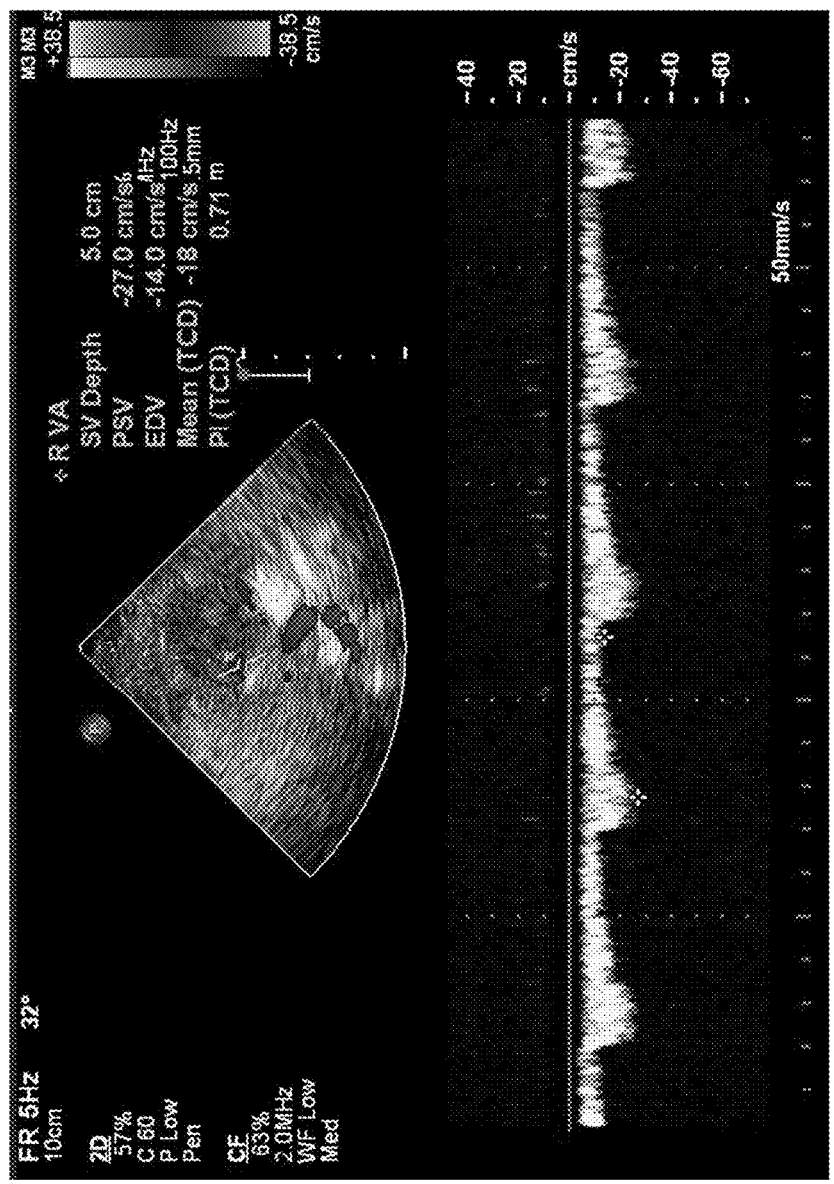
FIG. 2 is a schematic view of analyzing image having a predetermined format.
Figure 3:
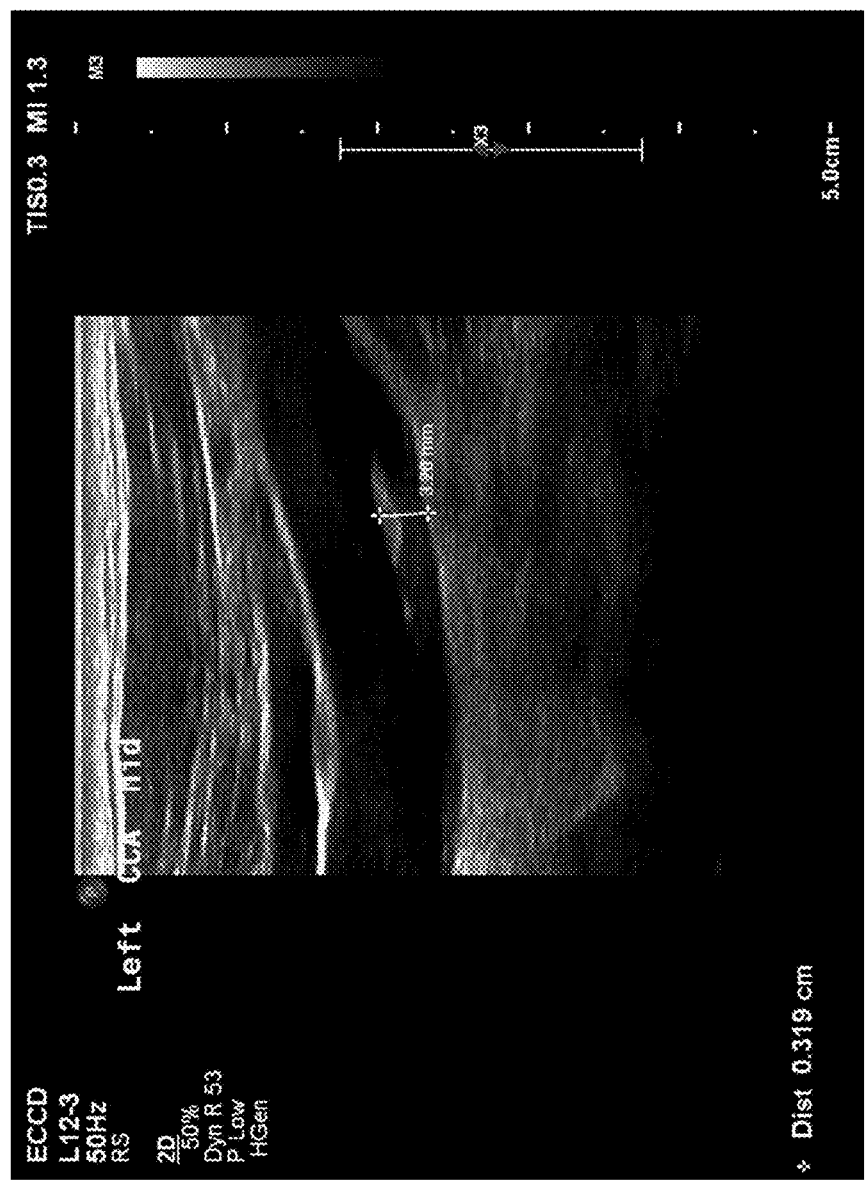
FIG. 3 is another schematic view of analyzing image having a predetermined format.
Figure 4:
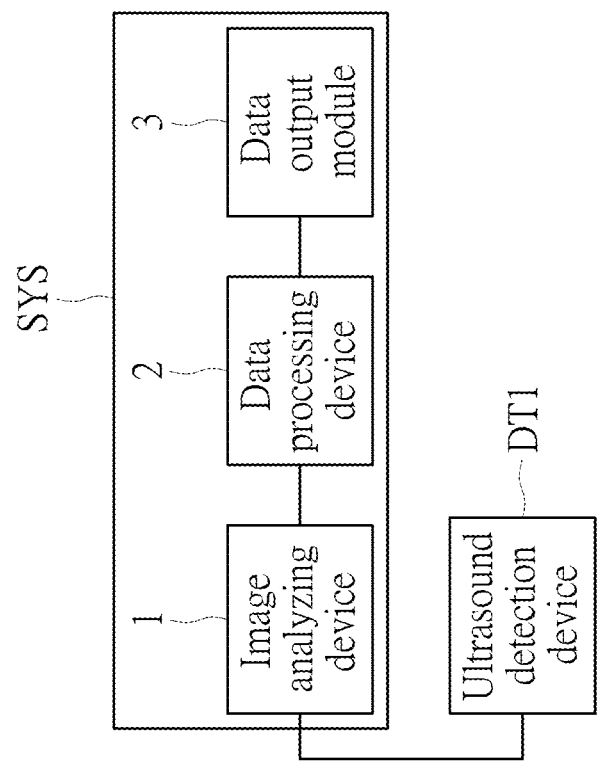
FIG. 4 is another schematic diagram of the ultrasound image recognition system according to the first embodiment of the present disclosure.
Figure 5:
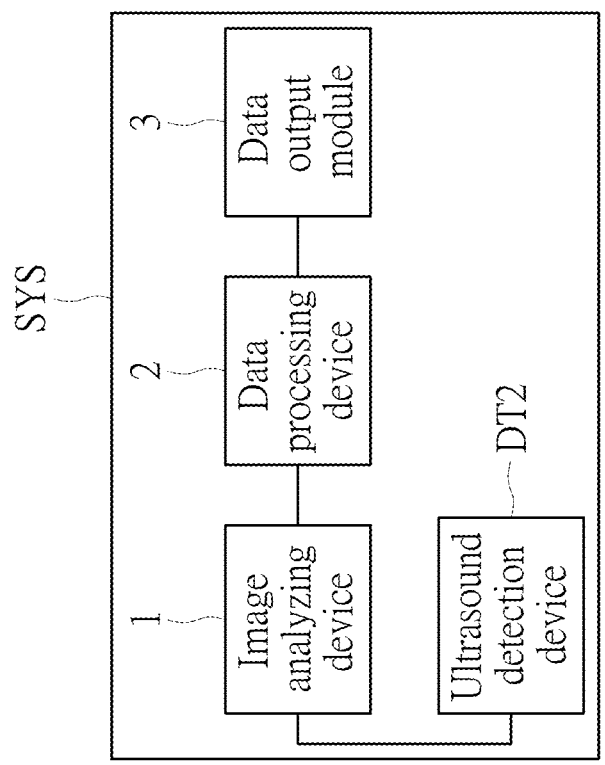
FIG. 5 is another schematic diagram of the ultrasound image recognition system according to the first embodiment of the present disclosure.

Referring to FIG. 1, FIG. 2, FIG. 3, FIG. 4, and FIG. 5, FIG. 1 is a functional block diagram of an ultrasound image recognition system according to a first embodiment of the present disclosure. FIG. 2 is a schematic view of analyzing image having a predetermined format. FIG. 3 is another schematic view of analyzing image having a predetermined format. FIG. 4 is another schematic diagram of the ultrasound image recognition system according to the first embodiment of the present disclosure. FIG. 5 is another schematic diagram of the ultrasound image recognition system according to the first embodiment of the present disclosure.

In this embodiment, an ultrasound image recognition system SYS is provided.

The ultrasound image recognition system SYS includes an image analyzing device 1, a data processing device 2, and a data output module 3. In this embodiment, the image analyzing device 1, the data processing device 2, and the data output module 3 can be disposed in a server (not shown in the figures), and these elements can also be disposed in a mobile device (not shown in the figures). Functions of the image analyzing device 1, the data processing device 2, and the data output module 3 can be achieved by software, hardware or firmware.

The image analyzing device 1 is configured to receive at least one image having a predetermined format IMG. The image having a predetermined format IMG is received from a digital imaging and communications in medicine image files (DICOM). The image having a predetermined format IMG is an image that conforms to a digital imaging and communications in medicine (DICOM) protocol. The DICOM is a universal standard protocol for the processing, storage, printing, and transmission of medical images. The DICOM contains the definition of file format and network communication protocol. The DICOM is an application protocol based on TCP/IP to communicate with various systems. Two medical instruments that can accept a DICOM format can receive and exchange images and patient data through files of the DICOM format. The DICOM can integrate medical image equipment, servers, workstations, printers and network apparatus from different manufacturers, so that they can be integrated in the digital image archiving and communication system (PACS).

Various instruments, servers, and workstations from different manufacturers support the DICOM format. That is, as long as an image is in the DICOM format, the ultrasound image recognition system SYS of this embodiment can perform analysis. However, the ultrasound image recognition system SYS of this embodiment mainly focuses on ultrasound images, so that the following descriptions are mainly provided for ultrasound images, specifically ultrasound images of blood vessels in a neck of a human body.

The image analyzing device 1 generates a plurality of physiological image parameters from a DICOM structured report according to at least one image having a predetermined format IMG, and the physiological image parameters at least include the following parameters:
(1) Peak systolic velocity (cm/s), PSV for short;
(2) End diastolic velocity (cm/s), ED for short;
(3) Mean velocity (cm/s), MV for short;
(4) Resistance index, RI for short, in which RI=(PSV−EDV)/PSV;
(5) Pulsation Index, PI for short, in which PI=(PSV−EDV)/MV; and
(6) Flow volume (ml/min), FV for short, in which FV=TAV*area*60 (seconds).

TAV is a time-averaged velocity, and area is a cross-sectional area of the blood vessel.

In addition, the image having a predetermined format IMG of this embodiment may be an ultrasound image of various parts of the human body. Therefore, the ultrasound image of each part, such as blood vessel image, and predetermined physiological parameters, are also different. The difference can be as follows:

After data comparison, the vertebral artery VA is adjusted to meet $PSV_{VA}>90$ cm/s or PI>1.2, and is determined as stenosis.

After data comparison, the basilar artery BA is adjusted to meet $PSV_{BA}>100$ cm/s or PI>1.2, and is determined as stenosis.

The parameters may be referred to as in the following table:

| | | |
|---|---|---|
| Middle Cerebral Artery (MCA), $PSV_{MCA}$ | >125 cm/s | MCA >50% Stenosis |
| Vertebral artery (VA) | | VA Stenosis |
| $PSV_{VA}$ | >90 cm/s | |
| Pulsation Index (PI) | >1.2 | |
| Basilar artery (BA) | | BA >50% |
| $PSV_{BA}$ | >100 cm/s | Stenosis |
| Pulsation Index (PI) | >1.2 | |

The data processing device 2 is connected to the image analyzing device 1. The image analyzing device 1 provides a plurality of physiological image parameters and the image having a predetermined format IMG to the data processing device 2. The data processing device 2 compares a plurality of physiological image parameters and a plurality of corresponding predetermined physiological image parameters to provide a comparison result of physiological parameters.

The data processing device 2 converts the image having a predetermined format IMG into an image having a first format. In this embodiment, the first format may be image formats such as jpg or bmp, etc., and is not limited in the present disclosure.

The data output module 3 is connected to the data processing device 2. The data processing device 2 provides images having a first format, a plurality of physiological image parameters, a plurality of predetermined physiological image parameters, and a comparison result of the physiological parameters to the data output module 3. The data output module 3 provides an ultrasound image analysis report based on the images having a first format, a plurality of physiological image parameters, a plurality of predetermined physiological image parameters, and a comparison result of the physiological parameters.

In this embodiment, the plurality of predetermined physiological image parameters are adjustable. In other words, the plurality of predetermined physiological image parameters can be adjusted based on experience or the recommendations of professionals in the relevant field. The adjustment can be as follows:
(1) The reference value for determining the degree of stenosis (Stenosis) of the middle cerebral artery (MCA) can be set according to decisions made by different users based on conditions of different patients. For example, $PSV_{MCA}$ are recommended to be set as $PSV_{MCA}>155$ cm/s, and pulsation index (PI) is recommended to be set as PI>1.2.

(2) At least 1.5% of internal carotid artery (ICA) stenosis reports require interpretations that combine images and data. The parameter $PSV_{ICA}$ is recommended to be set as $PSV_{ICA}>125$ cm/s. The parameter resistance index (RI) is recommended to be set as RI>0.75.

(3) A vertebral artery (VA) stenosis report needs to be interpreted by the resistance index (RI), the blood flow (Flow), or the vascular diameter (Diameter). The resistance index (RI) is recommended to be set as RI>0.75. The blood flow (Total Flow) is recommended to be set as Total Flow<100, vascular diameter (Diameter) is recommended to be set as Diameter<0.26.

Referring to FIG. 2 and FIG. 3, in this embodiment, it can be observed whether there is atherosclerotic plaque formation on the inner wall of the carotid artery by using the image having a predetermined format IMG, and a type and a location of the plaque can also be confirmed. Furthermore, a thickness of these plaques and a degree of blood vessel stenosis caused by the plaques can be measured.

A direction of blood flow, whether the blood flow is regular or turbulent, the diameter of the blood vessel, and the blood flow can be determined based on a color Doppler technology.

In addition, in other embodiments, the ultrasound image recognition system SYS can also be connected to a server S1. That is, the ultrasound image recognition system SYS also includes a communication device 4. The communication device 4 is configured to communicate with the server S1.

The data processing device 2 provides the image having a first format, the plurality of physiological image parameters, the plurality of predetermined physiological image parameters, and the comparison result of the physiological parameters to the server S1.

Another ultrasound image recognition system (not shown in the figures) can also provide a corresponding image having a first format, a plurality of corresponding physiological image parameters, a plurality of corresponding predetermined physiological image parameters, and a corresponding comparison result of physiological parameters to the server S1. That is, the plurality of ultrasound image recognition systems SYS can provide locally detected ultrasound images, analyzed physiological image parameters, and analyzed physiological parameter comparison results to the server S1.

The server S1 can execute a big data analysis that had personal data removed to generate a plurality of adjusted predetermined physiological image parameters according to the images having a first format, the plurality of physiological image parameters, the plurality of predetermined physiological image parameters, and the comparison results of the physiological parameters provided by the ultrasound image recognition system and the another ultrasound image recognition system. The server S1 can periodically provide the plurality of adjusted predetermined physiological image parameters to the ultrasound image recognition system SYS and the another ultrasound image recognition system (not shown in the figures).

Furthermore, in this embodiment, the data output module 3 includes a storage unit 31. A plurality of analysis report templates R1 are stored in the storage unit 31. The ultrasound image analysis report is processed according to one of the analysis report templates R1.

In addition, since each ultrasound image corresponds to a user, the data processing device 2 can also receive user information corresponding to at least one image having a predetermined format IMG.

In addition, as shown in FIG. 4, the ultrasound image recognition system SYS of this embodiment can also be connected to an ultrasound detection device DT1. The ultrasound detection device DT1 may be a handheld wireless ultrasound scanner.

That is, the ultrasound image recognition system SYS can be disposed in a mobile device to be connected to the ultrasound detection device DT1 for execution of real-time image detection and image analysis. The ultrasound detection device DT1 can be connected to the ultrasound image recognition system SYS in a wired communication manner or in a wireless communication manner. That is, the ultrasound detection device DT1 is disposed at an exterior of the ultrasound image recognition system SYS.

In other embodiments, as shown in FIG. 5, an ultrasound detection device DT2 is included in the interior of the ultrasound image recognition system SYS, and the ultrasound detection device DT2 is connected to the image analyzing device 1. That is, the ultrasound detection device DT2 can be built-in in the ultrasound image recognition system SYS.

Second Embodiment

Figure 6:
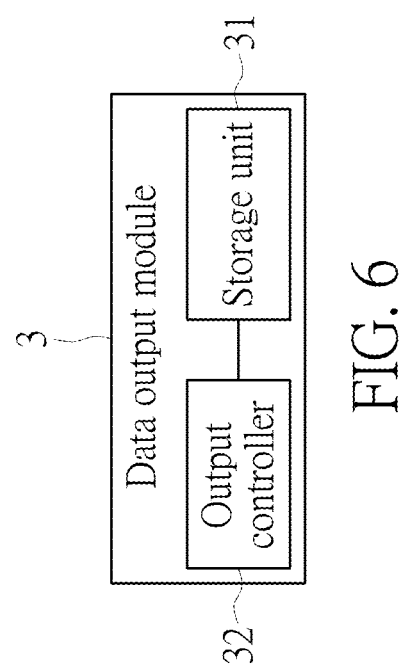
FIG. 6 is a schematic diagram of a data output module according to a second embodiment of the present disclosure.
Figure 7:
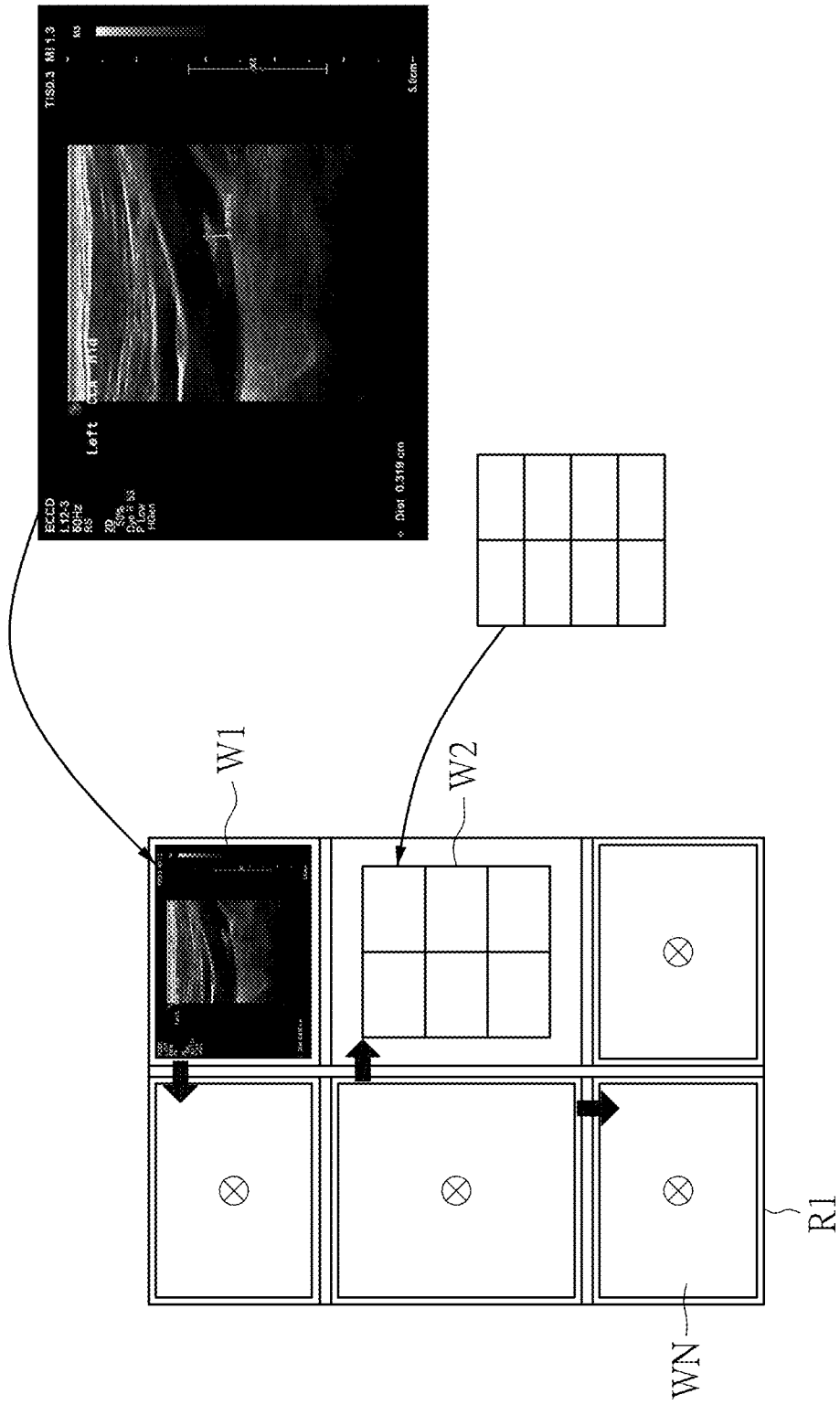
FIG. 7 is a schematic diagram of the data output module configured to output an analysis report according to the second embodiment of the present disclosure.

Referring to FIG. 6 and FIG. 7, FIG. 6 is a schematic diagram of a data output module according to a second embodiment of the present disclosure, and FIG. 7 is a schematic diagram of the data output module configured to output an analysis report according to the second embodiment of the present disclosure.

In this embodiment, the data output module 3 is implemented by hardware. The data output module 3 includes a storage unit 31 and an output controller 32. The storage unit 31 stores a plurality of analysis report templates R1. The storage unit 31 is connected to the output controller 32.

Each of the analysis report templates R1 includes a plurality of editing areas W1 to WN. When the image having a first format, the plurality of physiological image parameters, the plurality of predetermined physiological image parameters, comparison results of physiological parameter, or the plurality of adjusted predetermined physiological image parameters are disposed in one of the plurality of editing areas W1 to WN of one of the analysis report templates R1, the image having a first format, the plurality of physiological image parameters, the plurality of predetermined physiological image parameters, comparison results of physiological parameter, or a size, a font size, and a table size of the plurality of images of the adjusted predetermined physiological image parameters are adjusted according to the size of the one of the plurality of editing areas W1 to WN.

That is, the image in the first format, the plurality of physiological image parameters, the plurality of predetermined physiological image parameters, the comparison results of physiological parameter, or the size and font size of the plurality of images of the adjusted predetermined physiological image parameters displayed in the data output module 3 can respectively include a default value. The information can be displayed on a display device according to their respective default values.

In addition, the plurality of editing areas W1 to WN of each of the analysis report templates R1 respectively include a predetermined size.

In this embodiment, when the image having a first format, the plurality of physiological image parameters, the plurality of predetermined physiological image parameters, the comparison results of physiological parameter, or the plurality of images of the adjusted predetermined physiological image parameters are disposed in one of the plurality of editing areas, the output controller 32 can enlarge or reduce the size of the image having a first format, the plurality of physiological image parameters, the plurality of predetermined physiological image parameters, the comparison results of physiological parameter, or the plurality of images of the adjusted predetermined physiological image parameters according to the size of the one of the plurality of editing areas, so that the image having a first format, the plurality of physiological image parameters, the plurality of predetermined physiological image parameters, the comparison results of physiological parameter or the plurality of images of the plurality of adjusted predetermined physiological image parameters are appropriately displayed in the one of the plurality of editing areas W1 to WN.

In addition, the text format, the image format, and the table format of the image having a first format, the plurality of physiological image parameters, the plurality of predetermined physiological image parameters, the comparison results of physiological parameters, or the plurality of adjusted predetermined physiological image parameters can be adjusted.

Furthermore, the plurality of editing areas W1 to WN of each of the analysis report templates R1 can be adjusted to a size that matches with a requirement of a user based on the predetermined size. Each analysis report template R1 can further be adjusted according to actual requirements. In other words, the users can use the specific analysis report template R1 to make adjustments to meet their own requirements. That is, the users can quickly create an analysis report template R1 based on customized requirements.

Beneficial Effects of the Embodiments

In conclusion, the ultrasound image recognition system provided in the present disclosure can provide fast and real-time ultrasound image analysis and provide data analysis services. In addition, the data output module of the ultrasound image recognition system can provide customized analysis report templates, and the data output module can further provide the function of automatically adjusting an image size, a text size, and a table size for quickly providing a customized report. Therefore, the ultrasound image recognition system and the data output module provided by the present disclosure can effectively reduce various costs associated with the provision of analysis reports.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An ultrasound image recognition system comprising:
an image analyzing device configured to receive an image having a predetermined format, wherein the image analyzing device generates a plurality of physiological image parameters based on the image having a predetermined format;
a data processing device being connected to the image analyzing device, wherein the image analyzing device provides the plurality of physiological image parameters and the image having a predetermined format to the data processing device, wherein the data processing device provides a comparison result of physiological parameters based on the plurality of physiological image parameters and a plurality of predetermined physiological image parameters, and the data processing device converts the image having a predetermined format into an image having a first format; and
a data output module being connected to the data processing device, wherein the data processing device provides the image having a first format, the plurality of physiological image parameters, the plurality of predetermined physiological image parameters, and the comparison result of physiological parameter to the data output module, and the data output module provides an ultrasound image analysis report based on the image having a first format, the plurality of physiological image parameters, the plurality of predetermined physiological image parameters, and the comparison result of physiological parameter.

2. The ultrasound image recognition system according to the claim 1, wherein the data output module includes a plurality of analysis report templates, and the ultrasound image analysis report is processed based on one of the plurality of analysis report templates.

3. The ultrasound image recognition system according to the claim 1, wherein the plurality of predetermined physiological image parameters are adjustable.

4. The ultrasound image recognition system according to the claim 1, wherein the ultrasound image recognition system is connected to a server, and the data processing device provides the image having a first format, the plurality of physiological image parameters, the plurality of predetermined physiological image parameters, and an comparison result of physiological parameters to the server, wherein another ultrasound image recognition system provides a corresponding image having a first format, a plurality of corresponding physiological image parameters, a plurality of corresponding predetermined physiological image parameters, and a corresponding comparison result of physiological parameters to the server, wherein the server executes a data analysis based on the images having a first format, the plurality of physiological image parameters, the plurality of predetermined physiological image parameters, and the comparison result of physiological parameters of the ultrasound image recognition system and the another ultrasound image recognition system to generate a plurality of modulated predetermined physiological image parameters, wherein the server periodically provides the plurality of modulated predetermined physiological image parameters to the ultrasound image recognition system and the another ultrasound image recognition system.

5. The ultrasound image recognition system according to the claim 1, wherein the data processing device further receives user information corresponding to the at least image having a predetermined format.

6. The ultrasound image recognition system according to the claim 1, wherein the ultrasound image recognition system is externally connected to an ultrasound detection device, the ultrasound detection device is connected to the image analyzing device of the ultrasound image recognition system, and the image analyzing device receives the at least one image having a predetermined format provided by the ultrasound detection device.

7. The ultrasound image recognition system according to the claim 1, further comprising an ultrasound detection device, wherein the ultrasound detection device is connected to the image analyzing device to provide the at least one image having a predetermined format, and the ultrasound detection device is disposed in the ultrasound image recognition system.

* * * * *